United States Patent [19]

Vollmer et al.

[11] 4,029,721
[45] June 14, 1977

[54] HALOGEN-CONTAINING PHOSPHORIC ACID POLYESTERS

[75] Inventors: Hartfrid Vollmer; Franz-Josef Dany, both of Erfstadt; Joachim Wortmann, Turnich; Peter Munch, Erfstadt, all of Germany

[73] Assignee: Hoechst Aktiengesellschaft, Frankfurt am Main, Germany

[22] Filed: Oct. 21, 1975

[21] Appl. No.: 624,546

[30] Foreign Application Priority Data

Oct. 26, 1974 Germany .................. 2451077

[52] U.S. Cl. ............... 260/928; 260/929; 260/930; 260/973; 260/986; 260/990
[51] Int. Cl.² .................. C07F 9/08; C07F 9/12
[58] Field of Search ............ 260/928, 929, 930

[56] References Cited

UNITED STATES PATENTS

| | | |
|---|---|---|
| 3,707,586 | 12/1972 | Turley .................. 260/928 |
| 3,803,272 | 4/1974 | Pivauver et al. .......... 260/928 X |
| 3,968,187 | 7/1976 | Morgan et al. ........... 260/928 |
| 3,978,170 | 8/1976 | Vollmer et al. .......... 260/928 X |
| 3,989,773 | 11/1976 | Turley et al. ........... 260/928 X |

FOREIGN PATENTS OR APPLICATIONS

| | | |
|---|---|---|
| 1,349,087 | 12/1964 | France ................. 260/928 |
| 2,356,034 | 5/1975 | Germany ............... 260/928 |
| 43-13259 | 9/1968 | Japan .................. 260/928 |

*Primary Examiner*—Richard L. Raymond
*Attorney, Agent, or Firm*—Connolly and Hutz

[57] ABSTRACT

Halogen-containing phosphoric acid polyesters of the general formula (I)

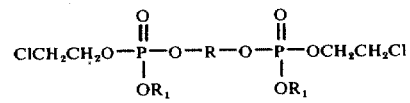

in which R stands for an alkylene radical or a halogen-substituted alkylene radical having from 2 to 6 carbon atoms, a —$CH_2CH_2$—O—$CH_2CH_2$— radical, a phenylene or an alkyl or halogenoalkyl-substituted diphenylenemethane radical, and $R_1$ stands for a branched or unbranched alkyl radical having from 6 to 18 carbon atoms.

14 Claims, No Drawings

HALOGEN-CONTAINING PHOSPHORIC ACID POLYESTERS

It is known that phosphoric acid chloroalkylesters of high molecular weight containing more than one phosphorus atom in the molecule can be used as flameproofing agents. Such esters and a process for making them have been described in German Patent Specification "Offenlegungsschrift"2,302,843, for example. The compounds described therein have the following general formula (A)

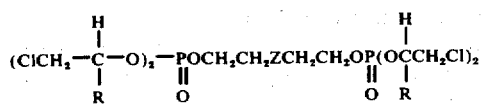

in which R stands for H, $CH_3$, $CH_2Cl$, Z stands for 0, $(OCH_2CH_2)_n0$ and n stands for a number between 1 and 6.

The process for making the compounds of the above formula (A) comprises first reacting glycols with an excess of phosphorus oxychloride to obtain bis-dichlorophosphates of the general formula (B)

and then reacting the bis-dichlorophosphates with an alkylene oxide in the presence of a catalyst and thereby transforming them into the compounds of formula (A).

A further process for making flame-retardant phosphoric acid esters has been described in German Patent Specification "Offenlegungsschrift" 2,338,007. This known process describes the preparation of tetrakis(2-halogenoalkyl)-alkylene-diphosphates and comprises
  a. reacting phosphorus trihalide with alkylene oxide in the presence of a tertiary amine hydrohalide-catalyst to give tris-(2-halogenoalkyl)-phosphite,
  b. reacting the tris-(2-halogenoalkyl)-phosphite with halogen to give bis-(2-halogenoalkyl)-phosphorus oxyhalide and alkylene dihalide, and
  c. reacting the mixture obtained as described under (b) with an alkyleneglycol to give tetrakis-(2-halogenoalkyl)-alkylene-diphosphate.

In order to obtain relatively pure, neutral final products, it is necessary for the crude products obtained by the above prior processes to be scrubbed with water or an aqueous solution of an acid or lye, and to be dried or distilled.

Needless to say such purifying procedure promotes partial hydrolysis of the products. As a result, they become increasingly acid in nature during storage and cease to be neutral, which is not desirable.

In addition thereto, the above prior processes can only be used for making such alkylene diphosphates as have four identical ester groups linked to the two phosphorus atoms.

In clear contrast with this, it is an object of the present invention to provide alkylene or arylene diphosphates which have two different ester groups linked to each of the two phosphorus atoms and which accordingly have specific beneficial properties. It is a further object of the present invention to provide a process for making these compounds.

The compounds of the present invention have the following general formula (I)

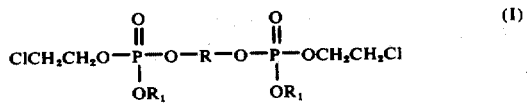

in which R stands for an alkylene radical having from 2 to 6 carbon atoms and being halogen substituted, if desired, a —$CH_2CH_2$—O—$CH_2CH_2$—radial, a phenylene or an alkyl or halogeno-alkyl-substituted diphenylenemethane radical and $R_1$ stands for a branched or unbranched alkyl radical having from 6 to 18 carbon atoms.

In those cases in which the substituent R in formula (I) stands for a halogenoalkyl-substituted diphenylenemethane radical, it is possible for chlorine or bromine to be used as the halogen. Preferably, however, the substituent R stands for an ethylene, hexamethylene or diethyleneglycol radical or for one of the following radicals

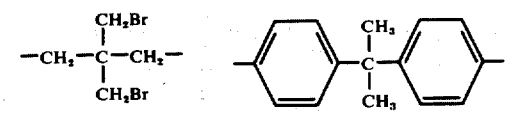

The invention comprises more specifically the following compounds having the following formulae:

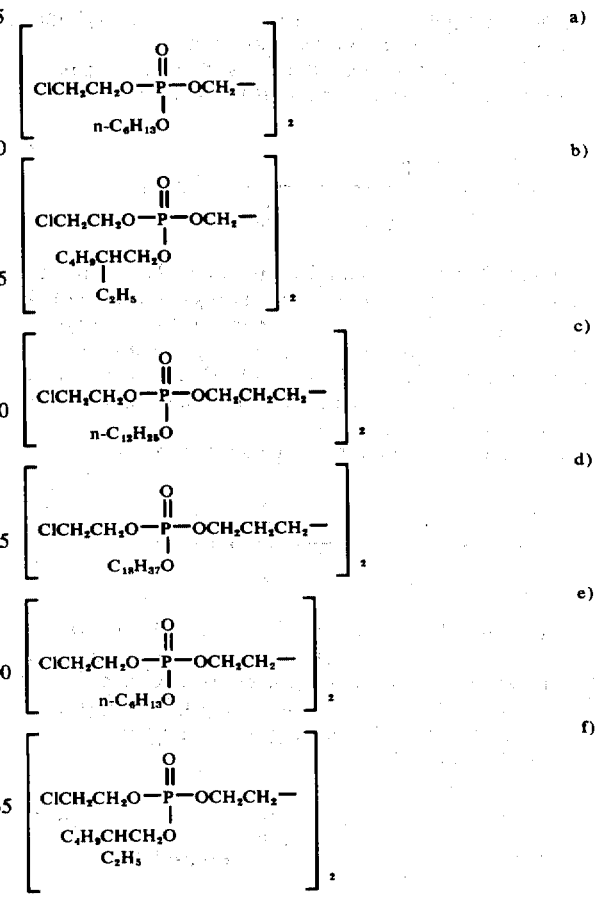

-continued

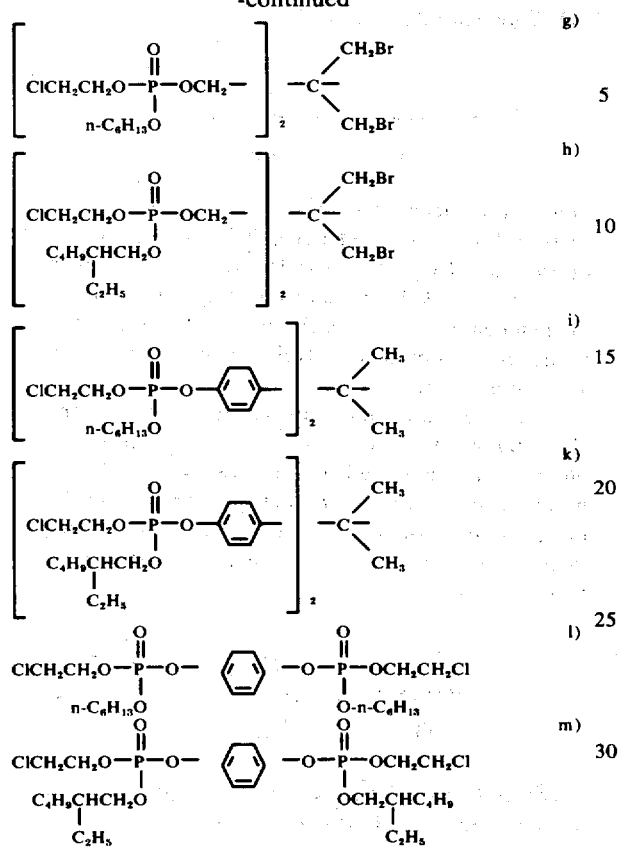

The compounds of the present invention are highly viscous, colorless and undistillable liquids.

The process for making the halogen-containing phosphoric acid polyester of general formula (I)

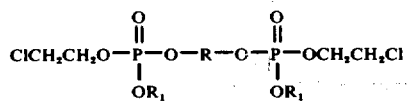
(I)

in which R stands for an alkylene radical having from 2 to 6 carbon atoms and being halogen-substituted, if desired, a —CH$_2$CH$_2$—O—CH$_2$CH$_2$—radical, a phenylene or an alkyl or halogeno-alkyl-substituted diphenylenemethane radical and R$_1$ stands for a branched or unbranched alkyl radical having from 6 to 18 carbon atoms, comprises:

a. reacting a compound of general formula (II)

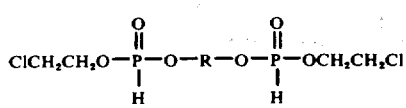
(II)

in which R has the meaning given above, with at least stoichiometric proportions of chlorine gas at temperatures within the range about 0° and 5° C in the presence of a solvent being difficultly soluble for hydrogen chloride to give a compound of general formula (III)

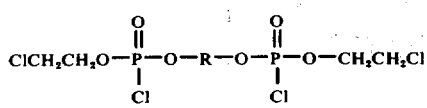
(III)

in which R has the meaning given above, terminating the reaction and freeing the reaction solution from chlorine gas in excess or resulting hydrogen chloride by introducing an inert gas thereinto, b. effecting the formation of the formula (I) compound by admixing the reaction solution from stage (a) at temperatures within the range about 15° and 50° C and while introducing further inert gas thereinto with a stoichiometric proportion of an alcohol of general formula (IV)

R$_1$OH  (IV), in which R$_1$ stands for a branched or unbranched alkyl radical having from 6 to 18 carbon atoms, terminating the reaction and distilling off the solvent, and c. freeing the crude product of general formula (I) from stage (b) from adhering hydrogen chloride by reacting the hydrogen chloride with at least stoichiometric proportions of ethylene oxide at a temperature within the range about 60° and 120° C, and purifying the crude product by distilling off ethylene chlorohydrin and ethylene oxide in excess.

The process of the present invention is more particularly used for making compounds of the general formula (I), in which the substituent R stands for an ethylene, hexamethylene or diethyleneglycol radical or one of the following two radicals

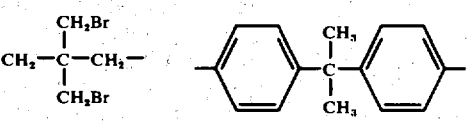

and R$_1$ stands for a n-hexyl, 2-ethylhexyl-, dodecyl or stearyl radical. In those cases in which the substituent R stands for a halogenoalkyl-substituted diphenylenemethane radical, it is preferably for chlorine or bromine to be used as the halogen substituents.

A further preferred embodiment of the process of the present invention comprises chlorinating the starting material in stage (a) in the presence of methylene chloride, dichloroethane or petroleum ether as a solvent. Hydrogen chloride which originates from this reaction may be expelled, for example, by the introduction of nitrogen so that the resulting intermediary product is substantially free from hydrogen halide.

The esterification of the above intermediary product in stage (b) may be effected at preferred temperatures within the range 40° and 50° C with the use, for example, of n-hexanol, 2-ethylhexanol, dodecanol or stearyl alcohol.

The crude product obtained in stage (b) should preferably be freed from hydrogen chloride with the aid of ethylene oxide at preferred temperatures within the range 80° and 120° C and in the presence of about 0.1–0.2 weight % of a disodium phosphate regulator, based on the quantity of the product of general formula (I). With respect to ethylene oxide, it is preferable for it to be used in proportions within the range 0.1 and 0.5 mol, for example, per mol of the product of general formula (I).

The general formula (II) compound used as starting material in the process of the present invention is known and can be made by the process described in U.S. Pat. No. 3,147,299, Examples 1 and 2.

In preparing the compounds of the present invention, it has been found advantageous to effect the reaction described hereinabove as a single pot reaction, leaving intermediary product unseparated. As a result of the specific method used for purifying the crude products with ethylene oxide, the final products are neutral and have an acid number of less than 1 mg of KOH/g substance. This is highly desirable for the storage of the products. In addition to this, the products are pure. This is due to the fact that the crude products are not purified with water, dilute acids are lyes (cf. German Patent Specifications "Offenlegungsschriften" 2,302,843 and 2,388,007) which means that undesirable partial hydrolysis of the crude products is avoided.

The products of the present invention are of commercial interest for use as flame-retardant softeners in polyvinyl chloride. They are more efficient than known compounds, e.g. tricresyl phosphate or liquid chlorinated paraffins containing 56 weight % of chlorine.

The following Examples illustrate the invention which is, however, not limited thereto.

EXAMPLE 1

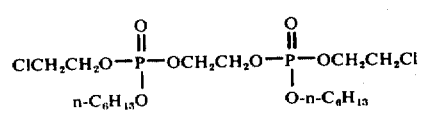

A solution of 670 g of $PCl_3$ (4.88 mol) and 1.5 l of methylene chloride was introduced into a reactor provided with reflux condenser and agitator and 303 g of ethylene-glycol (4.88 mol) was added dropwise with agitation at room temperature. The reaction was complete after about 1 hour. After that time, a further 2.44 mol of ethylene-glycol was added to the reaction mixture so that the reaction temperature remained within the limits of 20°–25° C. Following this, chlorine was introduced at 0°–5° C into the solution obtained until the solution assumed a yellow-green coloration which indicated the end of the reaction. Chlorine gas in excess and resulting chlorohydrocarbon were expelled by means of nitrogen. The introduction of nitrogen was continued and 498 g (4.88 mol) of n-hexanol was added at room temperature. After all had been added, the temperature was increased for a period of about 1 hour to 48° C, the solution was distillatively freed from the solvent and a highly viscous clolorless liquid was obtained as the residue. It was admixed at 90° C first with 1 g of $Na_2HPO_4$ and then with ethylene oxide until continuous reflux after about 15–30 minutes indicated that ethylene oxide ceased to be absorbed. 0.75 mol of ethylene oxide underwent reaction. Ethylene oxide in excess and resulting ethylene-chlorohydrin were distilled off under vacuum. The distillation residue was the phosphoric acid ester having the formula indicated above. It had an acid number of less than 1 mg of KOH/g substance and was obtained in a yield of 97% of the theoretical.

The ester was analyzed and the following results were obtained:

| | Found: | Calculated: |
|---|---|---|
| P | 11.1 % | 10.8 % |
| Cl | 13.3 % | 12.4 % |

EXAMPLES 2 to 10

The procedure was the same as that described in Example 1. Compounds of the following formula

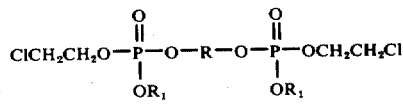

in which the substituents R and $R_1$ have the meanings given in Table I hereinafter, were made. The products obtained in each particular case were identified by elementary analysis. The results obtained are indicated in Table I.

Table I:

| Example | R | $R_1$ | Analysis Found | Calculated |
|---|---|---|---|---|
| 2 | $-CH_2CH_2-$ | $-CH_2CH-C_4H_9-$<br>$\quad\quad\ \ \|$<br>$\quad\quad\ \ C_2H_5$ | 11.1 % P<br>13.3 % Cl | 10.8 % P<br>12.4 % Cl |
| 3 | $-(CH_2)_6-$ | $n-C_{12}H_{25}-$ | 7.3 % P<br>9.1 % Cl | 7.4 % P<br>8.5 % Cl |
| 4 | $-(CH_2)_6-$ | $n-C_{18}H_{37}-$ | 6.5 % P<br>8.1 % Cl | 6.8 % P<br>7.8 % Cl |
| 5 | $-CH_2CH_2-O-CH_2CH_2-$ | $n-C_6H_{13}-$ | 10.5 % P | 11.8 % P |
| 6 | $-CH_2CH_2-O-CH_2CH_2-$ | $-CH_2-CH-C_4H_9-$<br>$\quad\quad\quad\ \|$<br>$\quad\quad\quad\ C_2H_5$ | 9.9 % P<br>12.3 % Cl | 10.5 % P<br>12.2 % Cl |
| 7 | $-CH_2-C(CH_2Br)_2-CH_2-$ | $n-C_6H_{13}-$ | 8.9 % P | 8.7 % P |
| 8 | $-C_6H_4-\underset{\underset{CH_3}{\|}}{\overset{\overset{CH_3}{\|}}{C}}-C_6H_4-$ | $n-C_6H_{13}-$ | 9.4 % P<br>10.8 % Cl | 9.1 % P<br>10.4 % Cl |
| 9 | $-C_6H_4-\underset{\underset{CH_3}{\|}}{\overset{\overset{CH_3}{\|}}{C}}-C_6H_4-$ | $-CH_2CH-C_4H_9-$<br>$\quad\quad\ \|$<br>$\quad\quad\ C_2H_5$ | 8.7 % P<br>9.9 % Cl | 8.4 % P<br>9.6 % Cl |
| 10 | $-C_6H_4-$ | $-CH_2CH-C_4H_9-$<br>$\quad\quad\ \|$<br>$\quad\quad\ C_2H_5$ | 9.7 % P | 10.0 % P |

EXAMPLE 11

The products of the present invention were tested as to their flame-retardant efficiency in polyvinyl chloride, their influence on the notched impact strength of polyvinyl chloride and their influence on the migration of the softener in the plastics. To this end, various polyvinyl chloride specimens, indentified as specimens A-E were prepared. Specimen A was free from flame-retardant agent, specimens B and C each contained a known flame-retardant agent and specimens D and E each contained a flame-retardant agent made in accordance with the present invention.

Specimens B-E having the flame-retardant agents incorporated therein were composed as follows (in parts by weight):

parts of suspension-made polyvinyl chloride having a K-value of 70,
1.05 part of a blend of 75 weight % of di-n-octyl tin mercaptide and 25 weight % of glycerol mono fatty acid ester,
0.105 part of p,p'-isopropylidene diphenol,
22.5 parts of dioctyl phtalate,
2.5 parts of epoxidized soybean oil, and
5.0 parts of flameproofing agent.

As regards composition, specimen A differed from specimens B-E by the fact that it was free from flame-retardant agent but contained 27.0 parts by weight of dioctyl-phthalate and 3.0 parts by weight of epoxidized soybean oil.

The individual powder blends were plasticized on a roller for 10 minutes at 160° C and made into sheets having the thickness necessary for the tests described hereinafter.

The migration of the softener in specimens A-E was tested as described in DIN test (German Industrial Standard) No. 59,407, process A. To this end, the specimens were made into round moulded plates 1 mm thick and 50 mm in diameter which were embedded in active carbon and stored for 24 hours at 100° C. After further storage for 24 hours at room temperature, the loss in weight in %, of the individual plates was determined.

The flexibility and freeze resistance of the products was identified by determining the notched impact strength at 0° and −10° C, respectively, in accordance with DIN test (German Industrial Standard) 53,453. High notched impact strength values mean high flexiblity.

The burn-up behaviour of the specimens was determined by the small burner test described in DIN text (German Industrial Standard) 53 438, which permitted the specimens to be categorized (burning classes K1, K2 or K3) and the individual burning classes to be further identified by burning time and burn-up length.

The test results obtained are indicated in the following Table II:

Table II

| Specimen | I | II | III | IV | V | VI |
|---|---|---|---|---|---|---|
| A | 3.3 | 6.1 | 2.7 | K3/0.2 mm | — | — |
| B | 2.1 | 3.3 | 1.9 | K3/0.2 mm | — | — |
| C | 3.0 | 4.0 | 2.9 | K1/0.2 mm | 48 | 140 |
| D | 2.2 | 9.3 | 2.9 | K1/0.2 mm | 1 | 60 |
| E | 2.1 | 3.1 | 1.9 | K1/0.2 mm | 1 | 61 |

In the above Table, the following symbols have the following meanings:
A: Polyvinyl chloride free from flame-retardant agent
B: Polyvinyl chloride containing tricresyl phosphate
C: Polyvinyl chloride containing liquid chlorinated paraffin (chloroparaffin) with 56 weight % of chlorine therein
D: Polyvinyl chloride containing the product of Example 6
E: Polyvinyl chloride containing the product of Example 9
Column I: Migration of softener (DIN-test 53 407)
Column II: Notched impact strength (DIN-test 53 453) identified at 0°C
Column III: Notched impact strength (DIN-test 53 453) identified at −10°C
Column IV: Burning class, sheet specimens 0.2mm thick
Column V: Burning period in seconds
Column VI: Burn-up length in mm The results indicated in the above Table II show that polyvinyl chloride specimens D and E having the flame-retardant agents of the present invention incorporated therein compare favorably with comparative specimens B and C, and that the initial properties of the specimens remain unaffected by the addition of the products of the present invention.

We claim:

1. Halogen-containing phosphoric acid polyesters of the general formula $$ClCH_2CH_2O-\underset{\underset{OR_1}{|}}{\overset{\overset{O}{\|}}{P}}-O-R-O-\underset{\underset{OR_1}{|}}{\overset{\overset{O}{\|}}{P}}-OCH_2CH_2Cl$$

in which R stands for an alkylene radical or a halogen-substituted alkylene radical having from 2 to 6 carbon atoms, a —CH$_2$CH$_2$O—CH$_2$CH$_2$— radical, a phenylene radical or a radical of the formula

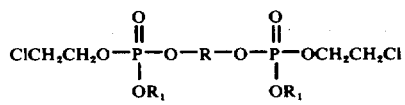

and R$_1$ stands for a branched or unbranched alkyl radical having from 6 to 18 carbon atoms.

2. Phosphoric acid polyesters as claimed in claim 1, wherein the substituent R stands for an ethylene, hexamethylene or diethyleneglycol radical or for a radical of one of the following formulas

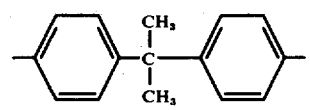

3. The compound of the formula:

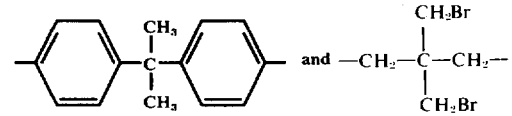

4. The compound of the formula:

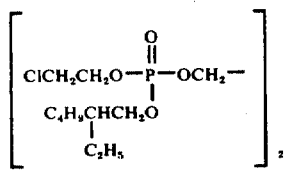
5. The compound of the formula:
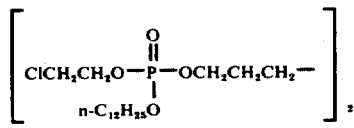
6. The compound of the formula:
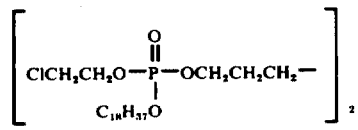
7. The compound of the formula:
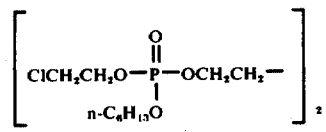
8. The compound of the formula:
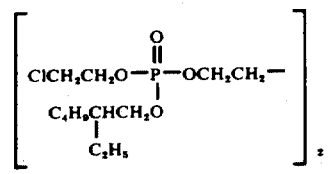
9. The compound of the formula:
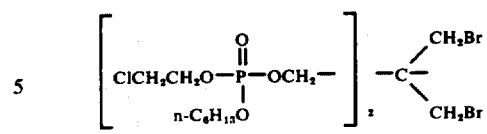
10. The compound of the formula:
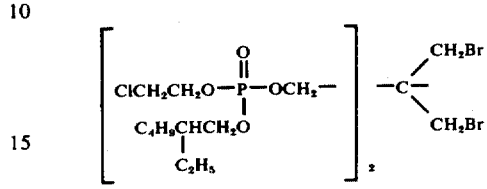
11. The compound of the formula:
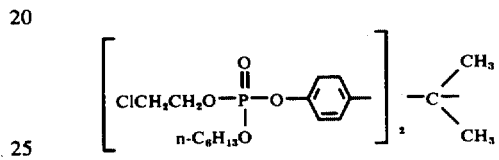
12. The compound of the formula:
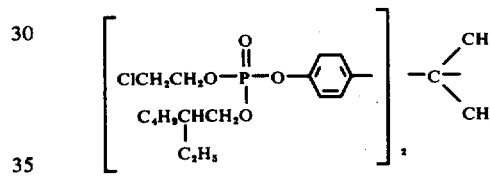
13. The compound of the formula:
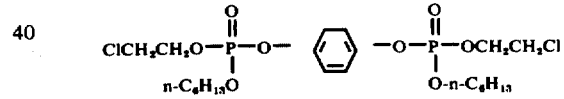
14. The compound of the formula:
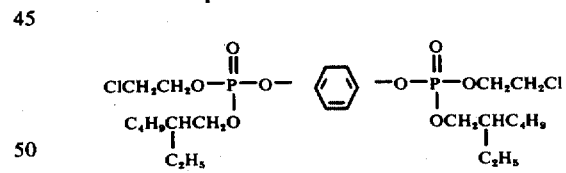
* * * * *